United States Patent [19]

Tokuyama et al.

[11] Patent Number: 5,346,697
[45] Date of Patent: Sep. 13, 1994

[54] ACTIVE OXYGEN SCAVENGER

[75] Inventors: Yoshie Tokuyama; Hiroshi Suzuki; Yoshihisa Matsuo; Eiko Takeuchi, all of Kagawa Ken, Japan

[73] Assignee: Soken Co., Ltd., Kagawa Ken, Japan

[21] Appl. No.: 885,724

[22] Filed: May 19, 1992

[30] Foreign Application Priority Data

Nov. 13, 1991 [JP] Japan .................................. 3-324029

[51] Int. Cl.$^5$ ............................................. A61K 35/78
[52] U.S. Cl. .................................. 424/195.1; 426/270; 426/271; 426/648; 426/800
[58] Field of Search ...................... 424/195.1; 426/278, 426/271, 648, 800

[56] References Cited

PUBLICATIONS

J. Carper, The Food Pharmacy, Bantam Books, Toronto, pp. 261–263, 1988.

*Primary Examiner*—John W. Rollins
*Attorney, Agent, or Firm*—Armstrong, Westerman, Hattori, McLeland & Naughton

[57] ABSTRACT

The present invention relates to an active oxygen scavenger which has been found to be contained in a water or organic solvent extract of rice. This active oxygen scavenger may be used as a medicament, beauty treatment, preservative or antibiotic.

17 Claims, 11 Drawing Sheets (a) BEFORE COATING (b) DIRECTLY AFTER COATING

ACTIVE OXYGEN SCAVENGER

FIELD OF THE INVENTION

The present invention relates to an active oxygen scavenger containing a water extract or an organic solvent extract of rice.

The active oxygen scavenger of the present invention is safe and can be used in a wide variety of fields, such as medicaments, foods, cosmetics, etc.

BACKGROUND OF THE INVENTION

When a human being keeps his body healthy, active oxygen (also referred to as superoxide or oxygen radicals) in the living body is always balanced with super oxide dismutase (SOD), which is an active oxygen scavenging enzyme, and the concentration of active oxygen is maintained at an almost constant value. However, at present, by an unbalanced diet, excessive stress, aging, etc., the formation of SOD is reduced and, on the other hand, by smoking, air pollution, etc., the content of active oxygen is increased.

As a result, thereof, excessive active oxygen exists in the living body which causes various tissue lesions. In particular, in the case of an aged person, the reduction of the SOD activity and the increase of the concentration of active oxygen causes lesions such as articular rheumatism and Behcet syndrome. Also, lipid peroxide formed by active oxygen becomes the main causative agent of modern diseases such as myocardial infarction, cerebral apoplexy, cataract, moth patches, freckles, wrinkles, diabetes mellitus, arteriosclerosis, a stiff neck, feeling of cold, etc.

Furthermore, even in the non-aged, since active oxygen is particularly liable to form at tissues such as skin, which are directly stimulated with environmental factors such as ultraviolet rays, etc., lesions such as the formation of melanine dyes, moth patches, and wrinkles, are liable to occur.

Thus, SOD for scavenging excessive active oxygen which causes the foregoing various lesions has become the subject of scientific and medical attention, and it has been attempted to utilize SOD as medicaments for the prophylaxis and treatment of these lesions or as an additive for cosmetics or foods. However, since SOD is unstable to heat and is inactivated by oral administration, and because SOD is very expensive, no one has yet succeeded in utilizing SOD an active oxygen scavenger.

Under the foregoing circumstances, active oxygen scavengers (including antioxidants having the same function as the SOD enzyme) have been investigated and active oxygen scavengers with a crude drug extract, etc., have been developed. However, such materials must be produced from specific raw materials and hence they are not only expensive but also cannot be stably supplied at present.

As described above, various investigations for scavenging active oxygen in a living body have been actively made since it was recognized that the foregoing various lesions were caused by active oxygen. Also, at present, with an increasing number of elderly and an increasing average life span, public attention is being focused on healthier living into old age. Additionally, from a viewpoint of a beauty treatment, active oxygen scavengers also have become the object of much public interest.

Accordingly, it has been desired to develop an active oxygen scavenger which is safe for the human being, inexpensive, excellent in its effect of scavenging active oxygen which causes various lesions as described above, can be easily produced, and also can be stably supplied.

SUMMARY OF THE INVENTION

The inventors have investigated various vegetable components with rice as the main subject. During the investigations, it has been discovered that rice contains components showing useful functions. Thus, the active oxygen scavenging effect with the water extract or the organic solvent extract of rice was measured, and as the result, it has been discovered that the extract has a very remarkable active oxygen scavenging effect and based on the discovery, the present invention has been accomplished.

That is, according to the present invention, there is provided an active oxygen scavenger containing a water extract or an organic solvent extract of rice.

Since rice has been used from old as a staple food in Japan, and now worldwide, and it has thus been established that the safety of rice is very high, an active oxygen scavenger (cited herein as the scavenger of the present invention) which is safe for the human body can be provided easily and at a low cost.

DETAILED DESCRIPTION OF THE INVENTION

Figure 1:
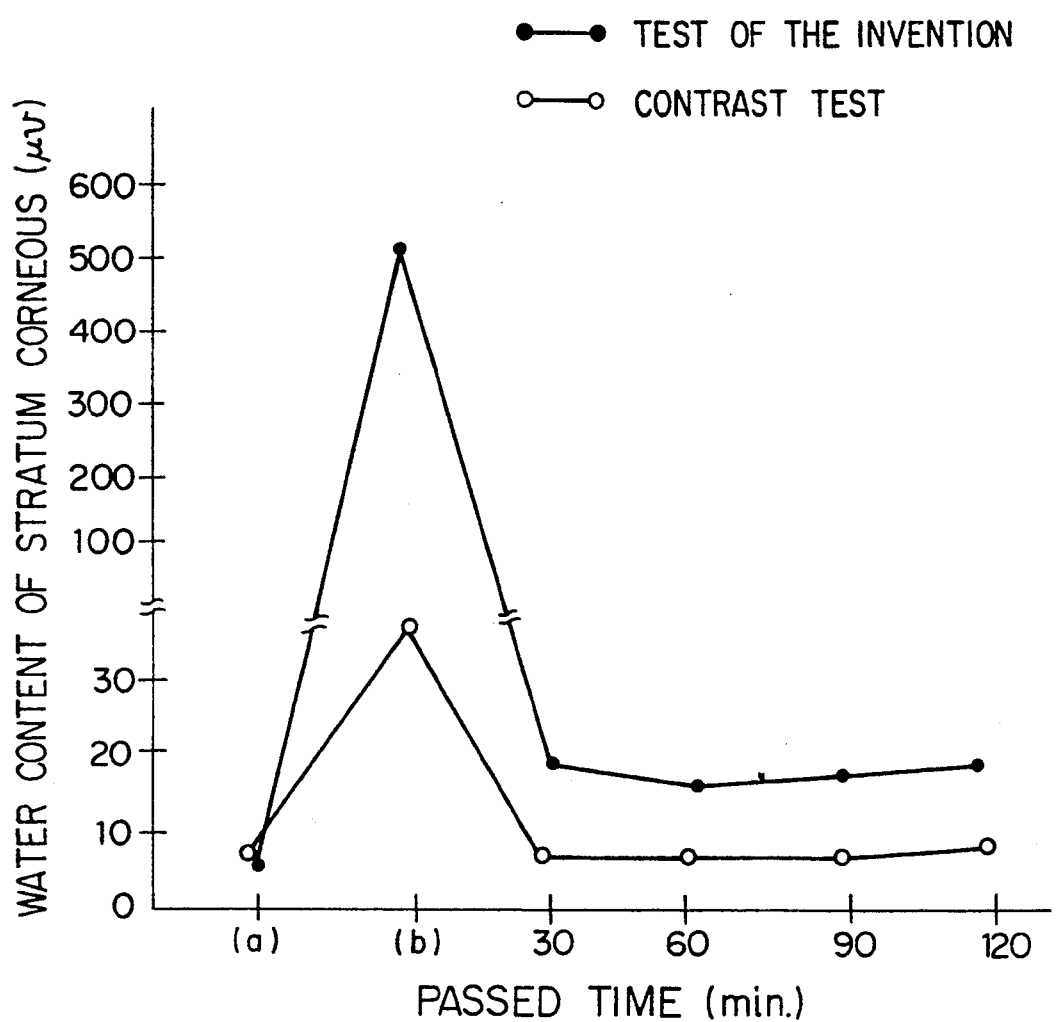
FIG. 1 is a graph showing the results of applying a single coating test using a moisture meter (SKICON 200, tradename) to evaluate the moisturizing effect of the scavenger of the present invention.

The present invention will now be described in detail with reference to the discussion below and Examples.

In the present invention, in the case of extracting rice with water or an organic solvent, when rice is ground or powdered, the surface area of rice is increased, whereby the extraction efficiency is greatly improved. This may be practiced by a general method using a grinder or a rice-cleaning machine. In this invention, it is not necessary to grind the rice but if it is not ground, it takes a long time to decompose the rice tissue and extract it.

For the water extraction, water is added to rice as it is or, preferably to ground or powdered rice. As to the addition amount of water, the amount of from 2 to 5 times the amount (by volume) of rice is enough. After adding water to rice, the mixture is heated and when the mixture comes a boiling state, the extraction is finished.

After finishing the extraction, by compressing and filtering the extract, a clear extract is obtained. In addition, the hot water may be added directly to the rice for carrying out the extraction.

The effective components extracted from rice have not yet been clarified, but since it has been confirmed that the unknown effective components are stable to heat, a high temperature is efficiently employed as the extraction temperature for the water extraction. However, when the temperature is low, the extraction of rice can be sufficiently practiced by carrying out the extraction for a longer time. When the extraction temperature is 40° C. or lower, it is necessary to carry out the extraction in an acidic state or an alkaline state, or by adding an antiseptic to the extraction system such that the rice does not rot. The extracting time may be few minutes in the case of the boiling extraction, but when the extracting temperature is an intermediate temperature (i.e., from the boiling point to about 40° C.), the extracting time of from about a few hours to about 24 hours is required. In the case of a lower temperature, the extracting time of from a few days to one month is required, although it depends upon the ground state of rice. However, in the latter case, it is more effective to heat the system lastly.

In the case of the water extraction, the most severe problem is the gelatination phenomenon of rice. If rice is gelatinized, not only is the extraction efficiency reduced but also the practical operation becomes very difficult. For preventing the occurrence of this trouble, it is proper to decompose the starch by adding amylase thereto to cause the reaction with the starch or acidifying the starch with the addition of hydrochloric acid. By employing these methods, the foregoing problem can be sufficiently solved and there is no problem in the practical operation.

Also, since it has been confirmed that the effective components extracted from rice are stable to acid and alkali, it is also effective to carry out an acid extraction or an alkali extraction of rice. Furthermore, in the case of the water extraction, a method of extracting rice after pre-treating rice with an acid or a base or after pre-treating by reacting with an enzyme (e.g., amylase) acting to the tissue of rice may be employed. Such a pre-treatment is considered to be effective since the effective components of rice become liable to be extracted by the application of the pre-treatment.

Moreover, it has been found that by an organic solvent extraction of rice, the extract having the foregoing effects of the present invention can be also obtained. This is very effective for making clear the effective components of this invention and for extracting the effective components of rice at a concentrated state, as well as for utilizing the effective components by compounding with other component(s) insoluble in water. In addition, as an organic solvent being used, it is preferred to use a solvent which is safe when it is administered to the human being, such as ethanol.

The water extract or the organic solvent extract obtained as described above may be subjected to a fermentation treatment such an alcoholic fermentation, a lactic acid fermentation, etc.

Rice is used as a staple food and it has never been considered to use rice as an active oxygen scavenger. Also, rice has been used as the raw material for rice wine (sake), rice spirit (shochu), vinegar, etc., but it has never been considered or practiced to extract rice. This is considered to be based on the fact that when rice is extracted by heating, rice is gelatinized (a known characteristic of rice) and hence the extraction of rice by heating is very difficult by the conventional knowledge.

Accordingly, the object of the present invention can be attained by using an organic solvent extraction, an acid or alkali extraction, or in the case of a water extraction, by acting amylase, etc., to facilitate the extraction.

By carrying out the sufficient extraction as described above, the effective components of rice as a very excellent active oxygen scavenger can be, for the first time, extracted.

The active oxygen scavenging effect of the active oxygen scavenger of the present invention is described below.

First, the effect of the scavenger of the present invention as a super oxide scavenger was determined.

The test was carried out by an NBT method.

Preparation of Reagent (1) 0.05 M $Na_2CO_3$ Buffer Solution (pH 10.2)

(2) 3 mM Xanthin Solution: In the buffer solution (1) was dissolved 45.6 mg of xanthin to provide 100 ml of a xanthin solution.

(3) 3mM EDTA Solution: In distilled water was dissolved 111.7 mg of EDTA (ethylenediaminetetraacetic acid)·2Na to provide 100 ml of an EDTA solution.

(4) BSA Solution: In distilled buffer solution was dissolved 15 mg of BSA (Bovine Serum Albumin) (made by Sigma Co.) to provide 10 ml of a BSA solution.

(5) 0.75 mM NBT Solution: In distilled buffer solution was dissolved 61.32 mg of NBT (nitro blue tetrazolium) to provide 100 ml of a NBT solution.

(6) Xanthin Oxidase Solution: Xanthin oxidase was diluted with distilled water to adjust it such that the absorbance in the air test of the operation method (analysis method) described below was in the range of from 0.2 to 0.23.

(7) 6mM $CuCl_2$ Solution: In distilled buffer solution was dissolved 102.26 mg of $CuCl_2·2H_2O$ to provide 100 ml of a $CuCl_2$ solution.

Operation Method (1) In a test tube was placed 2.4 ml of the $Na_2CO_3$ buffer solution and then, 0.1 ml of the xanthin solution, 0.1 ml of the EDTA solution, 0.1 ml of the BSA solution, and 0.1 ml of the NBT solution described above were added to the buffer solution.

(2) Then, 0.1 ml of a solution of an extract sample was added to the mixture, and after allowing the resultant mixture to stand for 10 minutes at 25° C., 0.1 ml of the xanthin oxidase solution described above was added thereto followed by stirring quickly and the mixture was incubated.

(3) After 20 minutes of incubation, 0.1 ml of the $CuCl_2$ solution described above was added thereto to stop the reaction and the absorbance was measured at 560 nm.

(4) For comparison, the same test was carried out on 0.1 ml of an aqueous solution of super oxide dismutase (Cu, Zn-type SOD, active 3000 to 4000 units/mg, made by Wako Junyaku K.K.) in place of the sample and the value obtained was defined as a super oxide scavenging ratio of 100%.

(5) Also, the same test was carried out using distilled water in place of the sample to provide a blank.

The measured results are shown in Table 1.

TABLE 1

| | Water Extract | Organic Solvent Extract | Alcoholic Fermentation After Water Extract | SOD |
|---|---|---|---|---|
| Super Oxide Scavenging Ratio (%) | 53 | 56 | 57 | 100 |

(Note:)
Water extract was obtained in Example 1.
Organic Solvent Extract was obtained in Example 3.
Alcohol fermentation product after water extraction was obtained in Example 4.

As is clear from the above results, it can be seen that the water extract and the organic solvent extract have a super oxide scavenging effect.

Then, the heat stability of the scavenger of the present invention was determined.

First, each of the scavenger of the present invention obtained in Example 1 and SOD was heat-treated for 10 minutes at 70° C. and the super oxide scavenging faculty of each of them was determined by the method described above.

The results obtained are shown in Table 2 below.

TABLE 2

| | Water Extract | Organic Solvent Extract | Alcoholic Fermentation After Water Extract | SOD |
|---|---|---|---|---|
| Super Oxide Scavenging Ratio (%) | 56 | 51 | 59 | 0 |

(Note:) Each extract was one obtained in each example as in Table 1.

As is clear from the above results, it can be seen that SOD is unstable to heat, while the scavengers of the present invention are all excellent in heat stability. Thus, is can be said that the effective components of the present invention capable of scavenging active oxygen are excellent in stability to heat.

Furthermore, the water extract obtained in Example 1 was concentrated thrice and the super oxide scavenging faculty of the concentrate was determined. The measurement of the super oxide scavenging ratio was carried out by the foregoing method. The results are shown in Table 3.

TABLE 3

| | Concentrate of Water Extract | SOD |
|---|---|---|
| Super Oxide Scavenging Ratio (%) | 93 | 100 |

(Note:) The concentration was carried out by a rotary evaporator.

As is shown above, it can be seen that by concentrating the scavenger of the present invention, the concentrated scavenger has almost the same super oxide scavenging effect as that of SOD.

Since the scavenger of the present invention shows a very remarkable active oxygen scavenging effect and is sanitary and safe, the scavenger can be utilized for medicaments, cosmetics, foods, etc., and hence these uses are explained below.

As a medicament, the scavenger of this invention can be used as an antiulcer agent. The test procedure for determining the antiulcer activity of the scavenger of this invention and the result thereof are as follows.

First, the activity of the scavenger of this invention to the ulcer induced by a restraint-cold stress in oral administration was determined. The procedure was carried out according to the Watanabe et al method. That is, after fasting a ddy male mouse of 8 weeks of age for 24 hours, 0.32 ml/mouse of the scavenger of this invention obtained in Example 1 shown below was orally administered. After 30 minutes, the mouse was placed in a stress gauge, and the mouse was immersed in water of 5° C. until the xiphopagus to apply thereto a restrained-cold stress. After 5 hours, the cervical vertebrae was dislocated to slaughter the mouse, and then, the stomach thereof was picked out. Thereafter, 1.5 ml of an aqueous 1% formalin solution was injected into the stomach, the stomach was further immersed in the aqueous 1% formalin solution to lightly fix the stomach tissue, and the stomach was allowed to stand as it was for 24 hours. Thereafter, the stomach was incised along the greater curvature, and the length (mm) of the injury formed at the gastric glands was measured and the sum total thereof per one mouse was shown as the ulcer coefficient. Also, as a control, a male mouse of the same age orally administered with an isotonic sodium chloride solution 30 minutes before placing the mouse in the stress gauge was used. In the test, a total of 15 mice were used in each case.

The results obtained are shown in Table 4 below.

TABLE 4

| | Administered Amount (ml/mouse) | Number of Test Mice | Mean Ulcer Coefficient |
|---|---|---|---|
| Isotonic Sodium Chloride Solution | 0.3 | 15 | 65.4 |
| Scavenger of the Invention | 0.3 | 15 | 29.1 |

As shown in Table 4, it can be seen that while the mean ulcer coefficient of the mice administered with an isotonic sodium chloride solution as a control is 65.4, the mean ulcer coefficient of the mouse administered with the scavenger of the present invention is 29.1, which shows clearly the oral administration of the scavenger of the present invention is effective as an antiulcer agent for ulcers induced by restraint-cold stress. As the result thereof, it has been found that the scavenger of the present invention shows an effective function as an antiulcer agent by directly acting from the mucous membranes of the stomach and intestines.

Next, the effect of the scavenger of the present invention to ulcers inducted by restraint-cold stress in a subcutaneous administration was determined. The method was carried out as in the case of the oral administration. That is, 15 mice each administered by subcutaneous injection with 0.3 ml/mouse of the scavenger of the present invention and 15 mice each administered by subcutaneous injection with an isotonic sodium chloride solution were allowed to stand for 30 minutes. Thereafter, they were placed in a stress gauge, and after applying thereto a restraint-cold stress, the effectiveness to ulcers inducted by restraint-cold stress by the subcutaneous administration of the scavenger of the present invention was determined.

The results obtained are shown in Table 5 below.

TABLE 5

|  | Administered Amount (ml/mouse) | Number of Test Mice | Mean Ulcer Coefficient |
| --- | --- | --- | --- |
| Isotonic Sodium Chloride Solution | 0.3 | 15 | 43.0 |
| Scavenger of the Invention | 0.3 | 15 | 22.7 |

As is clear from the results shown in Table 5, it can be seen that the mean ulcer coefficient of 15 mice each administered by subcutaneous with 0.3 ml/mouse of an isotonic sodium chloride solution is 43.0, while the mean ulcer coefficient of 15 mice each administered by subcutaneous with 0.3 ml/mouse of the scavenger of the present invention is 22.7, which shows the effectiveness of the scavenger of the present invention as an antiulcer agent by subcutaneous administration.

From the results described above, it has been found that the scavenger of the present invention is effective to ulcers by stress in both the oral administration and the subcutaneous administration.

Next, the effectiveness of the scavenger of the present invention to an ethanolic ulcer which is one of the ulcers occurring by directly acting to the mucous membrane of stomach as an antiulcer agent was determined by an oral administration. Since it has been confirmed as described above that the scavenger of the present invention is effective to stress ulcers in oral administration and in subcutaneous administration, oral administration only was carried out in this test. The test of the ethanolic ulcers was carried out according to the Robert et al's method. That is, after fasting a Wister/ST series male rat of eight weeks of age for 24 hours and abstaining the rat from water for 16 hours, 1.0 ml/rat of a solution obtained by dissolving 5 g of the scavenger of the present invention obtained in Example 2 in 10 ml of an isotonic sodium chloride solution was orally administered to the rat. After 30 minutes, the cervical vertebrae was dislocated to slaughter the rat, and then the stomach thereof was picked out. Thereafter, 10 ml of an aqueous 1% formalin solution was injected into the stomach, the stomach was immersed in the aqueous 1% formalin solution to lightly fix the stomach tissue, and the sum total of ulcers generated at the gastric glands was measured as the ulcer coefficient as in the case of mice. Also, in this case, rats orally administered with an isotonic sodium chloride solution were also used as control. In the test, 15 rats were used for each test.

The results obtained are shown in Table 6 below.

TABLE 6

|  | Doses (ml/rat) | Number of Rats Tested | Mean Ulcer Coefficient |
| --- | --- | --- | --- |
| Isotonic Sodium Chloride Solution | 1.0 | 15 | 48.1 |
| Solution of Scavenger of the Invention | 1.0 | 15 | 19.1 |

As is clear from the results shown in Table 6, it can be seen that while the mean ulcer coefficient in the rats orally administered with an isotonic sodium chloride solution as a control is 48.1, the mean ulcer coefficient in the rats orally administered with 1.0 ml/rat of the scavenger of the present invention is 19.1, and hence the scavenger of the present invention is an effective antiulcer agent for the ethanolic ulcer occurring by directly acting on the mucosa membrane of a stomach.

Also, the scavenger of the present invention can be utilized as a skin therapeutic agent. The scavenger of the present invention was coated twice (morning and evening) to the affected parts of panelists having various kinds of skin diseases every day and after continuing the coating therapy for one month, the affected parts were diagnosed.

The results are shown in Table 7 below.

TABLE 7

|  | Significant Improvement | Useful | Slightly Useful | Nothing to Say | Stop | Useful Ratio (%) |
| --- | --- | --- | --- | --- | --- | --- |
| Abrasion, Wound | 1 | 4 | 6 | 2 | 0 | 84.6 |
| Burns | 2 | 6 | 5 | 1 | 0 | 92.9 |
| Diaper Rash | 1 | 4 | 6 | 1 | 0 | 91.7 |
| Insect Sting | 1 | 6 | 4 | 2 | 0 | 84.6 |
| Boil, Pimple | 0 | 7 | 13 | 3 | 0 | 87.7 |
| Acne | 8 | 7 | 5 | 2 | 0 | 90.0 |
| Chaps, Cracks | 3 | 4 | 3 | 1 | 0 | 90.9 |
| Xeroderma | 4 | 15 | 7 | 2 | 0 | 92.9 |
| Itching of Skin | 2 | 7 | 15 | 2 | 0 | 92.3 |
| Eczema | 3 | 5 | 7 | 2 | 0 | 88.2 |
| Atopic Dermatitis | 3 | 10 | 6 | 5 | 0 | 79.2 |
| T. Maculo-vesiculosa | 0 | 3 | 5 | 0 | 0 | 100.0 |
| Tinea-Pedis | 0 | 6 | 2 | 0 | 0 | 100.0 |

(Note) 1. The scavenger of this invention obtained in Example 1 was used.
(Note) 2. The useful ratio was the ratio of the sum total of Significant Improvement + Useful + Slightly Useful.
(Note) 3. The Evaluations were made by special medical doctors.
(Note) 4. Panelists: 40 men and 45 women. Average age: 30.5 (ages 1 to 87).

As shown above in Table 7, since the scavenger of the present invention has the effects as various skin therapeutic agents, it can be seen that the scavenger has a fibroblast activating activity and further an antimicrobial activity.

Also, since the scavenger of the present invention is useful for xeroderma, acne, etc., it can be seen that the scavenger also has a moisturizing effect and an effect of properly restraining the increase of skin lipids. The test method of practically determining the moisturizing effect and the effect of properly restraining the increase of skin lipids, and the results thereof are as follows.

First, for illustrating the power of the moisturizing effect of the scavenger of the present invention, a single coating test was carried out using a moisture meter (SKICON 200, tradename, made by Soken Co., Ltd.). As the measuring conditions, the circumstances of a room temperature of 20° C. and a relative humidity of 65% were selected and the panelists were rested under the foregoing circumstances about 10 minutes before the measurement. As the test portions flexural sides of forearms (both arm sides) having no efflorescence of skin were selected.

The test was carried out by five panelists suffering from xeroderma.

The mean values of the changes of the water content of the main test (using the scavenger of the present invention obtained in Example 1) and the contrast test (using water) read from the moisture meter are shown in FIG. 1 of the accompanying drawings.

The measurement method of the single coating test was as follows:

1) A test portion of $5 \times 5$ cm$^2$ and a contrast portion of $5 \times 5$ cm$^2$ were selected on the antebrachial bent side of each panelist.

2) The water content of the stratum corneum of each portion was measured.

3) The water content of the stratum corneum was measured directly after coating the sample or 30 minutes, 60 minutes, 90 minutes, or 120 minutes after coating the sample.

From the results shown in FIG. 1, in the case of coating the scavenger of the present invention, in the water content of the stratum corneum, an increase of about 10 times that in the contrast was observed directly after coating. Also, it was seen that in the case of after 30 minutes to 120 minutes since coating, the portion coated with the scavenger of the present invention kept water of an amount of from 2 to 3 times that in the contrast case until 120 minutes.

Then, for numerically providing the medical treatment effect of a xeroderma by the scavenger of the present invention, an in vivo water absorption-desorption test before using the scavenger of this invention and after 2 weeks since the use of the scavenger was carried out using a moisture meter (SKICON 200). The panelists were the same five panelists used in the case of obtaining the mean values shown in FIG. 1 and the measurement condition carried out in this case was the same as that in the foregoing single coating test.

Figure 2:
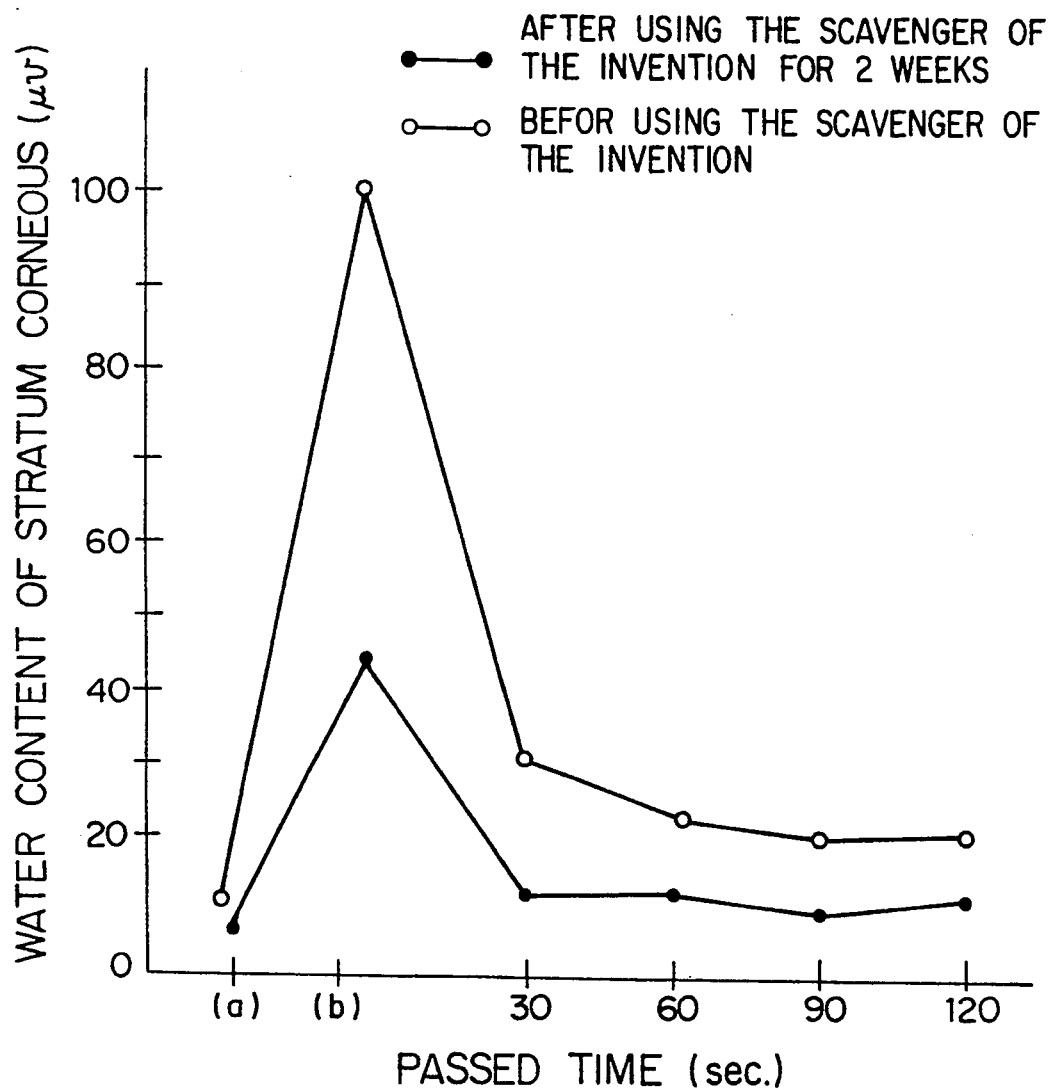
FIG. 2 is a graph showing the results of applying a water absorption-desorption test before using the scavenger of the present invention and after using the scavenger for two weeks.

In addition, for the evaluation of the effect, a contrast test (the measurement at the portion uncoated with the scavenger of this invention) was always carried out such that the evaluation of the main test was not influenced by the seasonal change of the water content of the stratum corneum of a living body. The water content of the stratum corneum was shown by the mean value of the five panelists. The results are shown in FIG. 2.

As the scavenger of the present invention, the product obtained in Example 1 was used.

Also, the measurement method in the in vivo water absorption-desorption test was as follows.

1) The water content of the stratum corneum at the test portion was measured.

2) One drop of distilled water was placed on the test portion and 10 seconds thereafter, the water drop was completely wiped away with a dry gauze.

3) The water content of the stratum corneum was measured directly after wiping away, or 30 seconds, 60 seconds, 90 seconds, and 120 seconds after wiping away.

As is shown in the graph of FIG. 2, it can be seen that by coating the scavenger of the present invention, both the water absorbing faculty of the skin (the value of the water content of the stratum corneum 0 second after water loading subtracted by the water content of the stratum corneum before water loading) and the water-keeping faculty (the curve showing the change of the water content of the stratum corneum from 0 second to 120 seconds after water loading) are simultaneously improved.

That is, in the skin before coating the scavenger of the present invention, the water content of the stratum corneum before water loading is very low (4.2 on an average) and the water absorbing faculty (40.8 on an average) is considerably lowered. Also, in regard to the water-keeping faculty, the stratum corneum of a normal man gradually releases absorbed water, while in the case of the panelists, after 30 seconds since water loading, the state of the stratum of the skin returns to the value before water loading. These results show that in the pathological stratum corneum, the water absorbing faculty, the water-keeping faculty, and the barrier function are all lowered. On the other hand, it has been confirmed that in the skin coated with the scavenger of the present invention, the water content of the stratum corneum before water loading and water absorbing faculty increase from 2 to 3 times and also the water-keeping faculty is considerably improved to almost same as that of a normal man.

From the above facts, it can be said that the scavenger of the present invention has an excellent effect for improving the water-containing state and the barrier function of the pathological stratum corneum. Also, by evaluating the scavenger of the present invention together with the moisturizing effect obtained by the single coating test, it can be said that the scavenger of the present invention has the moisturizing effect of imparting to the stratum corneum the properties of increasing the water absorbing faculty and water-keeping faculty of the stratum corneum, absorbing a large amount of moisture from outside and retaining water once absorbed.

Figure 3:
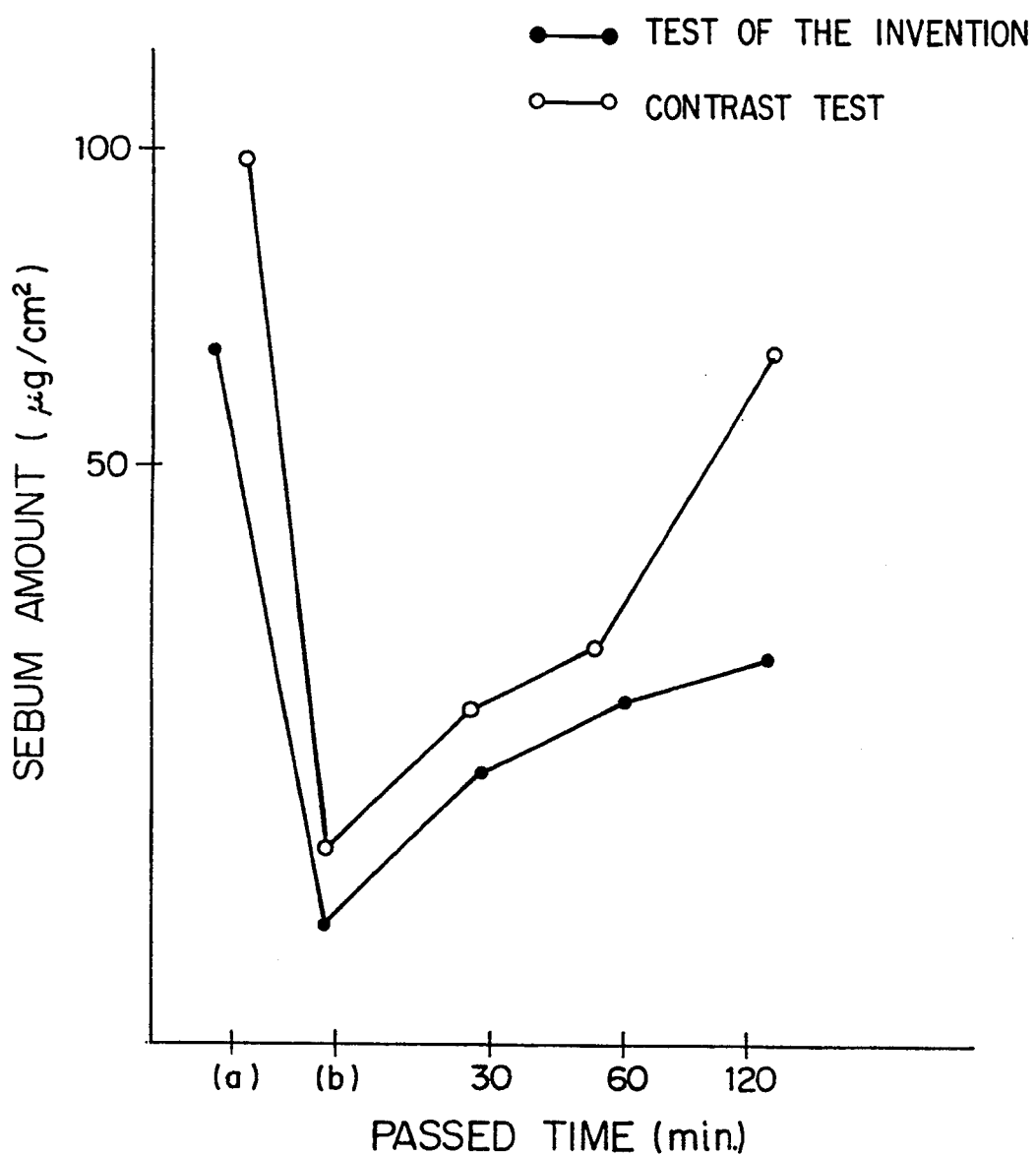
FIG. 3 is a graph showing the results of testing the change of the amount of skin lipids in the case of coating the scavenger of this invention after washing a face and in the case of only washing a face.

Furthermore, for experimentally illustrating the secretion-inhibiting effect of the amount of skin lipids by the scavenger of the present invention, the change of the amount of skin lipids after face washing was measured. As the panelists, five panelists randomly selected from the panelists used for making the results shown in Table 7 above were used and the mean value of the change of the amount of skin lipids in the main test (coating the scavenger of this invention after face washing) and in a contrast test (face washing only) is shown in FIG. 3. In addition, as the scavenger of the present invention, the product obtained in Example 1 was used.

As shown in FIG. 3, it has been found that by coating the scavenger of the present invention, the increase of the sebum amount is considerably restrained. By the sebum amount secretion-restraining effect of the scavenger of this invention, the prophylaxis and treatment effect for acne is supported.

Moreover, by the following test, it has been clarified that coating of the scavenger of this invention on a skin as cosmetics gives the effect of smoothening and fining the skin.

The scavenger of this invention was coated on the right arm portion of each panelist twice a day for one month and the portion coated with the scavenger of this invention was measured by a kinematic friction meter. As a contrast, the same portion of the left arm was used. The test was made by six panelists.

The measurement conditions were as follows:

| | |
|---|---|
| Temperature: | 25° C. |
| Humidity: | 60% |
| Sensor: | KES-SE Friction Tester SR-2 Type (0.5 mm piano wire used) |
| Friction Static Load: | 50 gf |
| Measuring Rate: | 1 mm/sec. |
| Measuring Distance: | 30 mm (integrated effective range 20 mm) |

Figure 4:
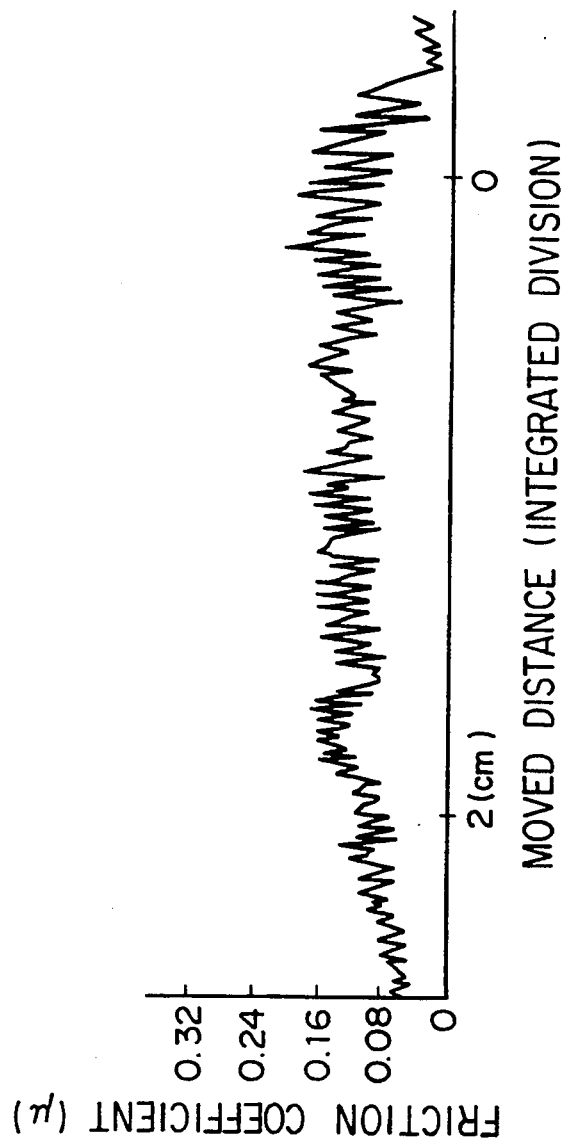
FIG. 4 is a graph showing the result of measuring the friction coefficient of the skin before coating the scavenger of the present invention.
Figure 5:
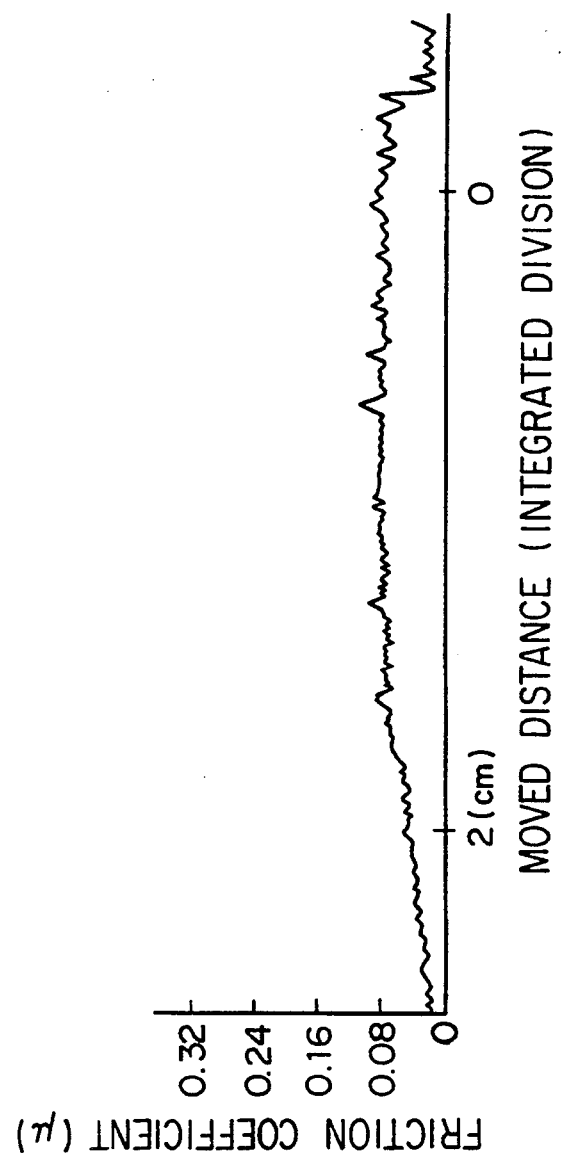
FIG. 5 is a graph showing the result of measuring the friction coefficient of the skin after coating the scavenger of the present invention for one week.

The results are shown in FIG. 4 and FIG. 5.

As shown in FIG. 4, in the portion of the left arm uncoated with the scavenger of the present invention, MMD (coefficient of variation) was 0.0172 but in the portion of the right arm coated with the scavenger of the present invention for one month, MMD was reduced to 0.0042 as shown in FIG. 5. The mean value of each of the six panelists was almost same. This is considered to be based on the fact that the variation by the unevenness of the surface is lowered, from which it has been found that the texture of the skin becomes fine.

In addition, when MIU (friction coefficient) was also determined at the same time, MIU before coating the scavenger of the present invention was 0.123 but was lowered to 0.073 in the skin after coating with the scavenger of the present invention for one month. Thus, it has been found that the scavenger of this invention also has an effect of smoothening a skin.

Furthermore, for illustrating the ultraviolet absorption effect of the scavenger of the present invention by data, the absorption spectrum of the scavenger of this invention was measured. The result is shown in FIG. 6.

Figure 6:
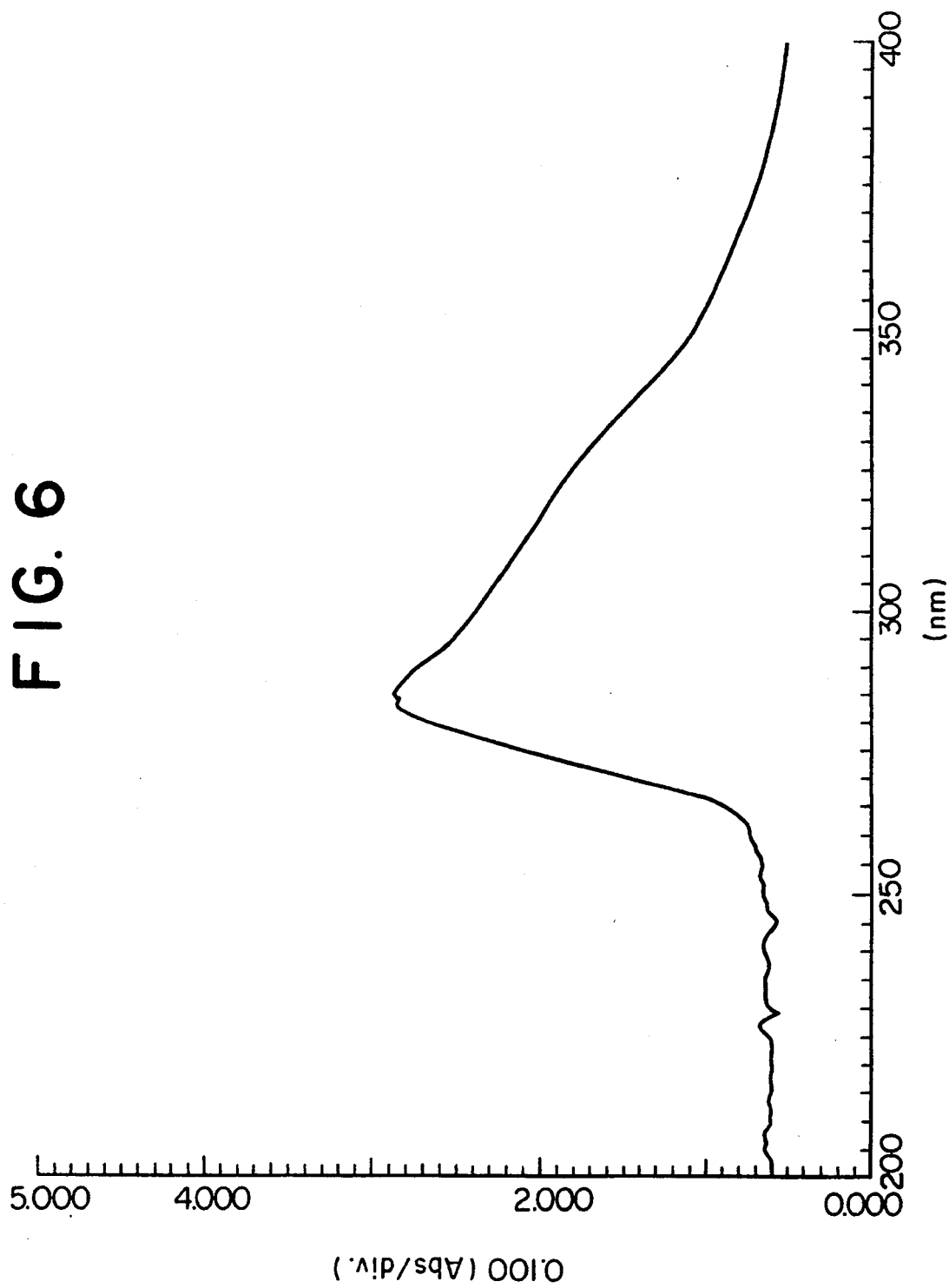
FIG. 6 is a graph showing the ultraviolet absorption spectrum of the scavenger of the present invention.

From the result shown in FIG. 6, it has been seen that the scavenger of the present invention is particularly excellent in the absorption effect in the low wavelength region (about 320 nm to 340 nm.) in the UVB region of from 280 nm. to 320 nm. and the UVA region of from 320 nm. to 380 nm.

Since the scavenger of the present invention does not have a sufficient absorption near the UBV region, it may be considered that the ultraviolet absorption effect of the scavenger is insufficient. However, it is said that the shortest wavelength of ultraviolet rays reaching the surface of the earth is 295 nm. and the longest wavelength thereof is from 320 nm. to 330 nm., and hence it can be said that the ultraviolet absorption faculty in a practical meaning is sufficient. The ultraviolet absorption faculty of the scavenger of the present invention is about thrice that of a crude drug extract and crude drug components (oil-soluble liquorice extract P-U (Spanish juice), licochalcone A, baicalein, $\tau$-oryzanol, etc.) having a natural ultraviolet absorption faculty, which are used at present. Thus, it has been proved that the scavenger of the present invention has an excellent ultraviolet absorption faculty. Furthermore, for illustrating the beautiful whitening action of the scavenger of the present invention, the test of tyrosinase activity hindering action was carried out.

The test procedures was as follows. That is, 1 ml of a substrate solution (aqueous 0.04% tyrosine solution) and 1 ml of a buffer solution (McIlvaine Buffer, pH 6.8) were correctly placed in an absorption cell and after correctly adding thereto 1 ml of water or 1 ml of the scavenger of the present invention obtained in Example 1, the resultant mixture was mixed by stirring at 35° C. After 5 minutes, the absorbance scale was set to the wavelength 475 nm to carry out a zero correction. Then, 0.02 ml of a tyrosinase solution (obtained by dissolving 5.3 mg of tyrosinase in an aqueous 0.9% NaCl solution) and the mixture was immediately stirred and incubated. The absorbance in this case was measured every 3 minutes.

The results obtained are shown in Table 8 below.

TABLE 8

| Minute | Water | Scavenger of the Invention |
|---|---|---|
| 0 | 0.007 | 0.016 |
| 3 | 0.063 | 0.057 |
| 6 | 0.152 | 0.081 |
| 9 | 0.243 | 0.097 |
| 12 | 0.329 | 0.112 |
| 15 | 0.419 | 0.127 |
| 18 | 0.497 | 0.141 |
| 21 | 0.560 | 0.152 |
| 24 | 0.617 | 0.163 |
| 27 | 0.637 | 0.175 |
| 30 | 0.646 | 0.184 |

From the measurement results shown in Table 8, it can be seen that the scavenger of the present invention has a tyrosinase activity hindering action. Thus, it can be said that the scavenger of the present invention has a beautiful whitening action.

Then, for determining the rejuvenating action of the skin by the scavenger of the present invention, the scavenger of this invention was coated on the back of the hand of each of six woman subjects of 70 to 80 years old for one week. The coated portion was sampled by a SUMP (Suzuki's Universal Micro-Printing) method, the microphotograph of the image by SUMP method was taken, and the result was compared with the skin uncoated with the scavenger of the present invention.

Figure 7:
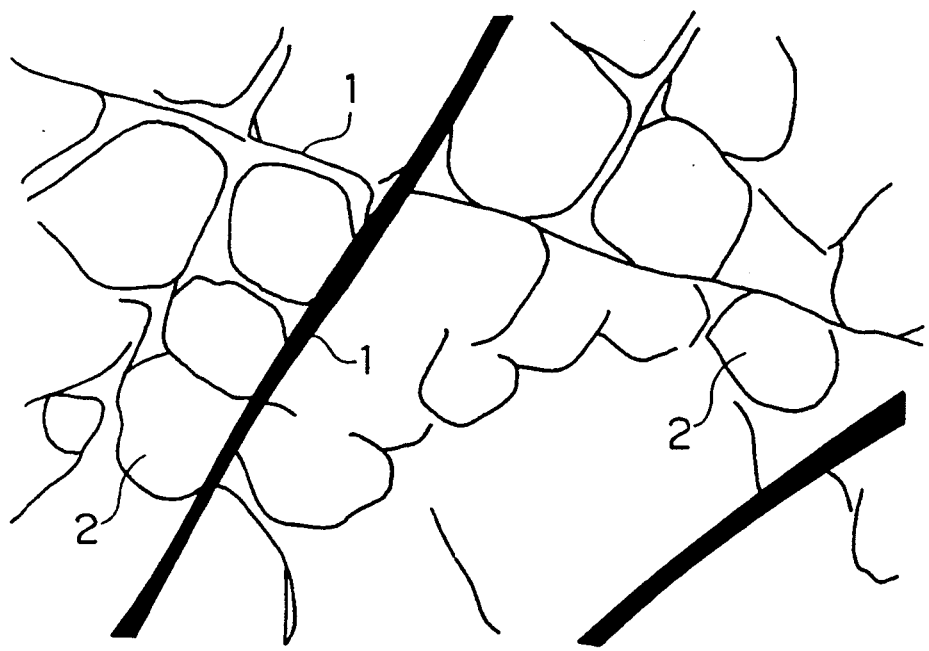
FIG. 7 depicts the furrows and the ridges of the skin of a woman subject twenty-one years old.
Figure 8:
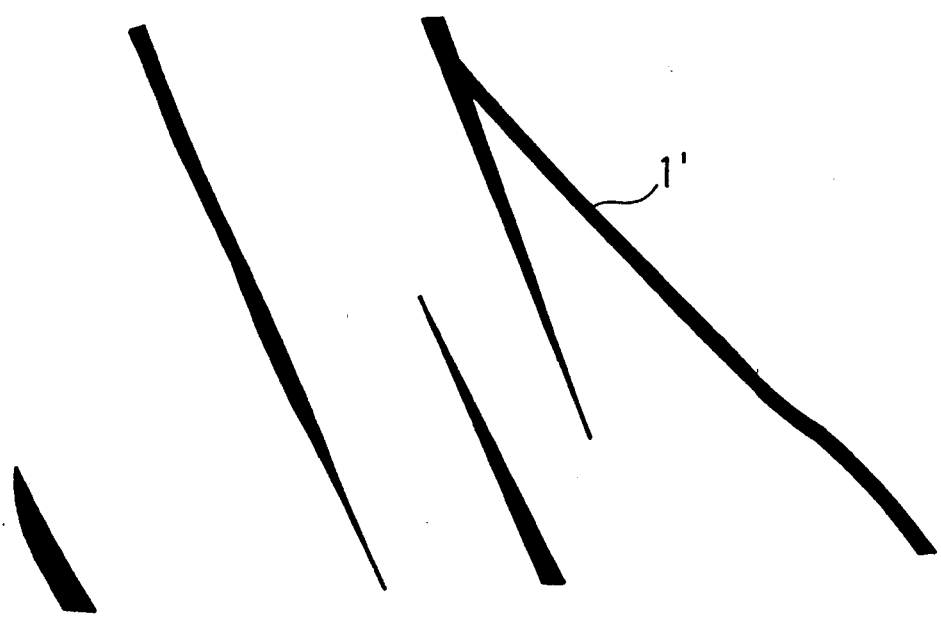
FIG. 8 depicts the furrows and the ridges of the skin of a woman subject seventy-one years old.

As shown in FIG. 7, in the skin of a woman subject of twenty-one years old, furrows 1 are clearly observed in many directions as well as ridge (carapace) 2 clearly appears. However, as shown in FIG. 8, in a subject of seventy-one years old, furrows 1' only are observed in one direction and no ridge is observed. It is said that with age, the skin loses the resilience, the furrows of the skin become shallow by stretching of the skin, and the ridge gradually disappears, and the same manner could be confirmed by the test.

Figure 9:
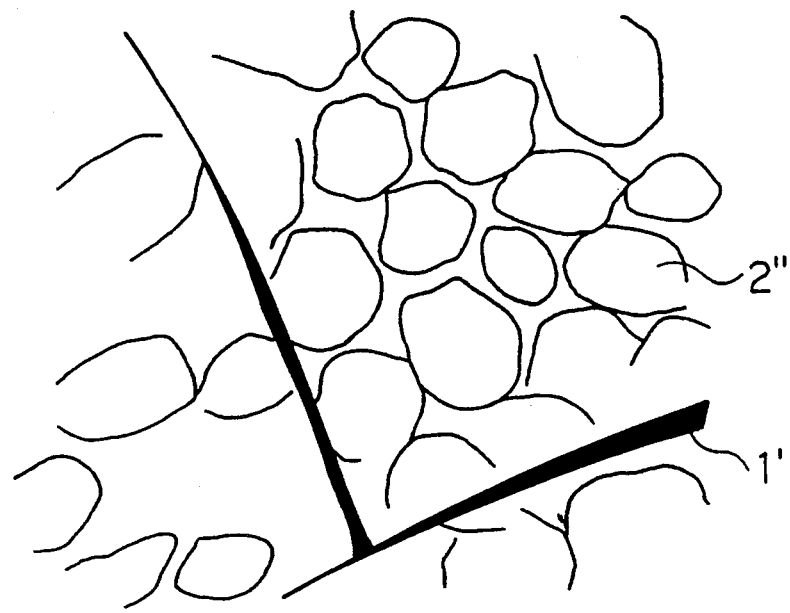
FIG. 9 depicts the furrows and the ridges of the skin of a woman subject seventy-one years old coated with the scavenger of the present invention for one week.

On the other hand, when the scavenger of the present invention was coated on the skin for one week, as shown in FIG. 9, the furrows which were observed in one direction only before coating the scavenger of this invention were clearly observed in many directions. Moreover, the ridge (carapace) 2' which was not observed in the subject of seventy-one years old was clearly observed and her skin became almost the same as the skin of the woman subject of twenty-one years old. Also, in feeling, the resilience was increased and the rejuvenating effect of the scavenger of this invention was confirmed. This phenomenon was also observed similarly on the remaining subjects. Thus, it can be said that by using the scavenger of the present invention, the essential function of the skin takes a turn for recovery and the clear and well-proportioned micro fingers inside the ridges appear. From the above facts, it has been proved that the scavenger of the present invention clearly has a rejuvenating action of the skin.

Then, for illustrating the aging preventing action of the scavenger of the present invention, the scavenger of the present invention was continuously coated on the back of the hand of each of three woman subjects of forty years old for one week and the coated portion was microscopically observed by a SUMP method. In this case, as the scavenger of the present invention, the product obtained in Example 1 was used.

Figure 10:
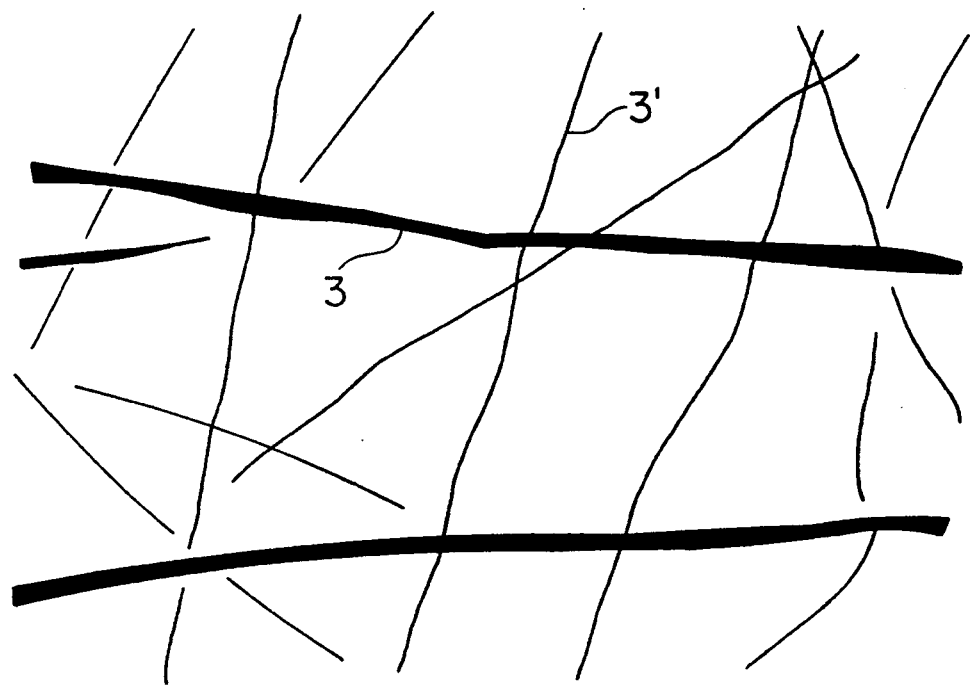
FIG. 10 is a view explaining the furrows and the ridges of the skin without being coated with the scavenger of the present invention.
Figure 11:
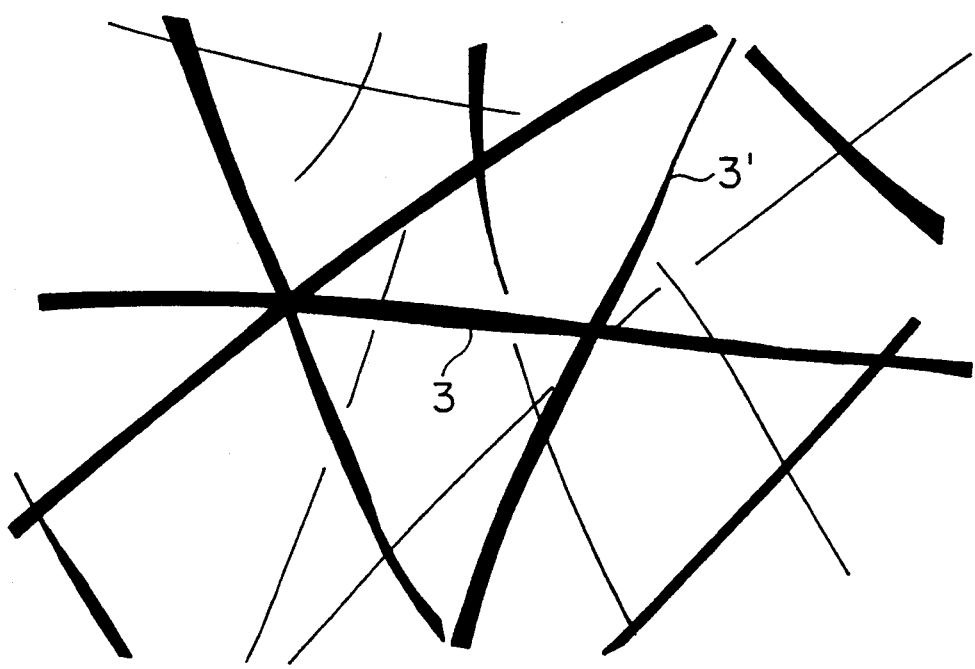
FIG. 11 is a view explaining the furrow and the ridge of the skin coated with the scavenger of the present invention for one week.

As shown in FIG. 10, in the skin uncoated with the scavenger of the present invention, the furrows 3 in one direction only were clearly observed and the furrows 3' in the direction crossing the direction of the furrow 3 were indistinct. On the other hand, in the skin continuously coated with the scavenger of the present invention for one week, as shown in FIG. 11, the furrows 3' which were indistinct clearly appeared as well as the fine furrows were observed. This phenomenon similarly appeared in the other two subjects. Thus, it has been proved that the scavenger of the present invention has an action for aging prevention of the skin.

Moreover, as described above, the scavenger of the present invention has the moisturizing effect capable of being used as medicaments. Thus, the scavenger of this invention satisfies all the actions as the bases of cosmetics and can be used in a wide field of applications such as creams, milky lotions, face lotions, cleansing creams, packs, soaps, etc.

Also, by drinking the scavenger of this invention, the same effects as described above are obtained.

Furthermore, it has been clarified by the following test that by adding the scavenger of the present invention to kitchen detergents, washing detergents, etc., the washing power and the foaming power are increased.

Figure 12:
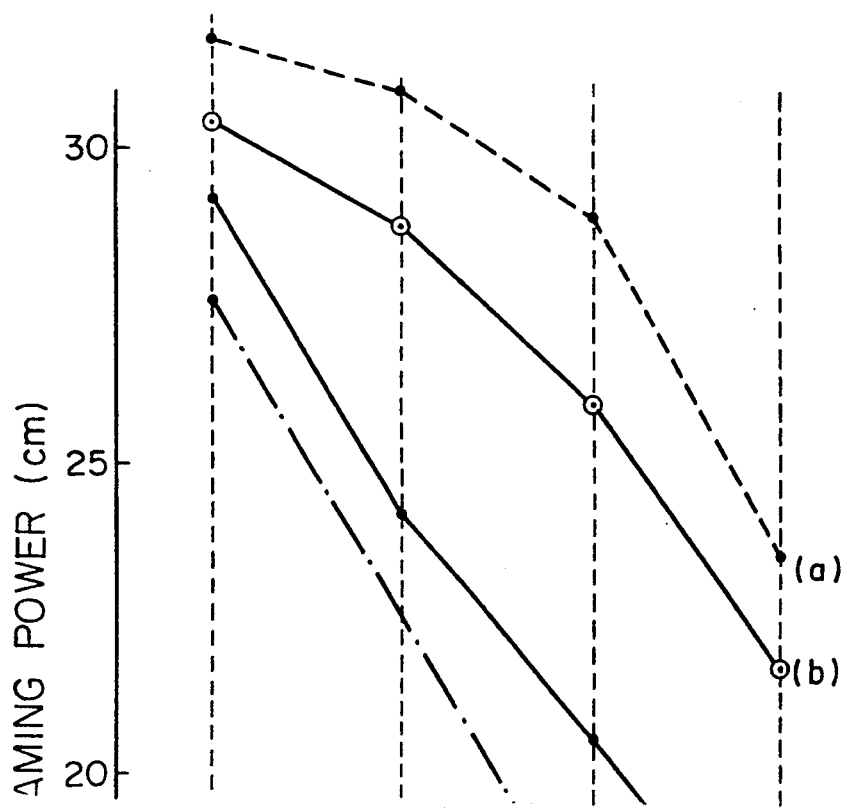
FIG. 12 is a graph showing the result of a foaming power test using a Ross-Miles test method.

The scavenger of the present invention (water extract of rice) was mixed with a base prepared such that the concentration of a surface active agent became 29% or 20% and then the concentration of the surface active agent was adjusted to 20%. As to the product obtained, a Leenerts test method as a detergent power test, a plate washing test method, and a Ross-Miles method as a foaming power test were carried out and the results obtained are shown in Table 9 and FIG. 12. The Ross-Miles test method and the Leenerts test method as the test methods were carried out according to the JIS standard. Also, the plate washing test method was carried out as follows. That is, a commercially available lard, a sponge (110 mm×75 mm×30 mm), a plate (diameter 25 cm), and 20 g of each sample (10 g of each detergent +10 g of city water) were prepared. First, 2.5 g of the commercially available lard was attached to the surfaces of one plate, the lard was spread out over the whole surfaces by a finger, and the plate was stored at about 25° C. The dry sponge was coated with 20 g of the sample, lightly crumpled to form foams, and the outside and the inside of the plate were washed each one round with the sponge. The washing operation was repeated 5 times for one plate, the test how many plates could be washed until the sponge was not bubbled was carried out 5 times, and the mean value was determined. The results are shown in Table 9 below.

TABLE 9

| Concentration of Surface Agent | Sample Name | | Plate-washing Method (No. of Plates) |
|---|---|---|---|
| 29% | Base only | 84.1 | 6.0 |
| 20% | Base only | 78.9 | 5.0 |
| 20% | Base + 20% Product of Invention in Example 1 | 89.0 | 7.2 |
| 20% | Base + 20% Product of Invention in Example 3 | 84.0 | 6.1 |

TABLE 9-continued

| Concentration of Surface Agent | Sample Name | Plate-washing Method (No. of Plates) |
|---|---|---|

(Note 1): The base is a mixture of polyoxyethylene lauryl ether sodium sulfate, coconut oil fatty acid amidopropylbetaine, laurylmethylamine oxide, and coconut oil fatty acid diethanol amide at a ratio of 21:7:2:3.
(Note 2): The concentration of the surface active is the concentration of the final product.

As is clear by comparing the cases of using the base only as the surface active agent with each other, when the concentration of the surface active agent (base) is lowered from 29% to 20%, the detergency and the foaming power are greatly reduced. However, by adding the scavenger (product) of the present invention, even by lowering the concentration of the surface active agent, the detergency and the foaming power are superior to the case of the concentration of the surface active agent (base) only of 29%.

The scavenger of the present invention can be also used as a bath product. A bath product is used by adding it to the bath water and taking a bath. When 50 ml of the scavenger of the present invention is added to 200 liters of warm water at 42° C. and 100 panelists took the bath, just after the bath, the skin was moist and smooth as compared with the case of taking a bath without using the scavenger of this invention.

Thus, for experimentally illustrating the warm bath effect (the effect of warming the human body completely and of being reluctant to chill after a bath) of the scavenger of the present invention, the skin surface temperature-maintaining effect after bath was investigated using a thermography apparatus. In this test, 15 panelists were used and the mean values of the skin surface temperatures of the main test (using the scavenger of this invention) read from the thermograph and the contrast test (using water only) are shown in Table 10 below.

TABLE 10

| | Before Immersion | (mean value of skin surface temperature) After Immersion (minutes) | | | | | | | |
|---|---|---|---|---|---|---|---|---|---|
| | | 2 | 5 | 10 | 15 | 20 | 25 | 30 | 40 |
| (A) | 31.9° C. | 35.0 | 34.6 | 34.5 | 34.2 | 33.9 | 33.6 | 33.3 | 32.7 |
| (B) | 31.9° C. | 35.2 | 35.0 | 34.8 | 34.5 | 34.3 | 34.1 | 33.9 | 33.6 |

(A): Bath of warm water only
(B): Bath containing the scavenger of the invention
In Table 10 above:
(Note 1): The scavenger of this invention used was the product obtained in Example 1.
(Note 2): The measurement method of the thermogram is described below.

In an inspection room having room temperature (20° C.±1° C.) and having no air flowing, the forearm of each panelist was adapted to the room temperature in the exposed state of the arm for about 30 minutes. Thereafter, the infrared rays radiated from the human body were detected and the thermogram of the upper back portion of the right forearm of the panelist was photographed using a thermographic apparatus for detecting the temperature information from the intensity of the infrared rays. Then, the right forearm of the panelist was immersed up to the elbow in a water bath (9 liters) kept at 41° C. for 10 minutes. The photographing intervals were 2 minutes, 5 minutes, 10 minutes, 15 minutes, 20 minutes, 25 minutes, 30 minutes, and 40 minutes after finishing the immersion of the arm, whereby the change of the temperature of the skin surface with the passage of time was observed.

As is clear from the results shown in Table 10, in the measurement results using the forearm portion as the measuring portion, the temperature difference between the case of taking the bath containing the scavenger of the present invention and the case of taking a bath of warm water only began to occur after 5 minutes and the temperature difference became 0.6° C. after 30 minutes. Also, in the data of each panelist with the passage of time, some panelists immediately showed the temperature difference after 2 minutes and other panelists showed the temperature difference after 10 to 15 minutes. However, all the panelists showed the temperature difference of from 0.5° C. to 1.5° C. after 40 minutes, which showed a very remarkable effect of the scavenger of this invention of maintaining warmth.

Also, when the forearm of each panelist was immersed in warm water containing a bath product mainly composed of sodium bicarbonate and Glauber's salt which were regarded as materials other than medicaments and the same test as above was carried out, no temperature difference between the case of using a bath of warm water only was observed by the immersion of the forearm only.

The scavenger of the present invention can be also utilized as preservatives and freshness-keeping agents for foods.

The antimicrobial test of the scavenger of the present invention to *Bacillus subtilis* and *Bacillus cereus* which are typical gram positive bacteria causing the spoilage of boiled rice, bread, etc., and *Escherichia coli* which is a typical gram negative bacterium and is considered to be a general indication of pollution, and the results thereof are as follows.

As a culture medium, 10 ml of an ordinary agar culture medium added with 1 ml of the scavenger of the present invention (the product obtained in Example 5) was used.

Also, as a control, 10 ml of an agar culture medium added with 1 ml of water in place of the scavenger of this invention was used. The cultivation was carried out at 35° C. and after 10 hours, 24 hours, 48 hours, and 72 hours, the growing state of each bacterium was observed.

The results obtained are shown in Tables 11 to 13.

TABLE 11

| Cultivation Time | *Bacillus subtilis* | |
|---|---|---|
| | Scavenger of the Invention | Water |
| 10 hours | − | ++ |
| 24 hours | − | ++ |
| 48 hours | − | +++ |
| 72 hours | − | +++ |

TABLE 12

| Cultivation Time | *Bacillus cereus* | |
|---|---|---|
| | Scavenger of the Invention | Water |
| 10 hours | − | ++ |
| 24 hours | − | +++ |
| 48 hours | − | +++ |
| 72 hours | − | +++ |

TABLE 13

| Cultivation Time | *Escherichia coli* | |
|---|---|---|
| | Scavenger of the Invention | Water |
| 10 hours | − | ++ |
| 24 hours | − | +++ |
| 48 hours | − | +++ |
| 72 hours | + | +++ |

(Note): Evaluation:
−: Not grown
+: Grown a little
++: Grown
+++: Greatly grown

As is clear from the results shown in Tables 11 to 13, in the culture medium added with water as a control, each bacterial culture grew greatly after the cultivation of 10 hours, while in the culture medium supplemented with the scavenger of the present invention, the growth of *Bacillus subtilis* and *Bacillus cereus* was completely hindered even after the cultivation of 72 hours. Also, in the culture medium supplemented with the scavenger of this invention, the growth of *Escherichia coli* was also observed after the cultivation of 48 hours or longer, but in this case, the scavenger of the present invention showed a large antimicrobial effect as compared with the control case.

The results of determining the preservative food-keeping effect of the scavenger of this invention using a steamed fish paste (kamaboko) of the ground fish meat of a white fish having a large protein content as a typical food and a sweet beverage made from fermented rice (amazake) as a typical drink were as follows.

First, to 200 g of the ground fish meat of the white fish having a large protein content was added the scavenger of the present invention in an amount of 10% 0 1% or 0 01% As the scavenger of the present invention, the product obtained in Example 5 described below was used. Also, the preservative effect on the same ground fish meat added with 1% water or 1% ethyl acetate as control was determined. In addition, ethyl acetate was sufficiently removed from the product in Example 5 but under the supposition that ethyl acetate might remain in the product, it was added as the control.

Each of the ground fish meats added with the scavenger of the present invention as described above was mashed well in an earthenware mortar disinfected with not water and shaped into a proper form. After steaming the ground fish meat in a steamer for 50 minutes, the steamed meat was allowed to stand at room temperature and the preservative effect thereof was observed with the passage of time (days) on threading by staling (hereinafter is referred to as threading) the color, the freshness, and the resilience thereof.

The results are shown in Table 14 below.

TABLE 14

| Additive | Amount (1%) | Conc.* (ppm) | Passed Days | | | | | | | | | | | |
|---|---|---|---|---|---|---|---|---|---|---|---|---|---|---|
| | | | 1 | 2 | 3 | 4 | 5 | 6 | 7 | 8 | 9 | 10 | 11 | 12 |
| Water** | 1.0 | — | − | − | ± | + | ++ | ++ | ++ | ++ | ++ | ++ | ++ | ++ |

TABLE 14-continued

| Additive | Amount (1%) | Conc.* (ppm) | Passed Days | | | | | | | | | | | |
|---|---|---|---|---|---|---|---|---|---|---|---|---|---|---|
| | | | 1 | 2 | 3 | 4 | 5 | 6 | 7 | 8 | 9 | 10 | 11 | 12 |
| Ethyl Acetate** | 1.0 | — | — | — | ± | + | ++ | ++ | ++ | ++ | ++ | ++ | ++ | ++ |
| Product of the Invention | 1.0 | 450 | — | — | — | — | — | — | — | — | ∓ | ∓ | ∓ | ∓ |
| | 0.1 | 45 | — | — | — | — | — | — | ∓ | ∓ | ∓ | ∓ | ∓ | ∓ |
| | 0.01 | 4.5 | — | — | — | — | — | ∓ | + | + | ++ | ++ | ++ | ++ |

*Concentration of the solid component of the scavenger of this invention.
**Control
(Note 1): Evaluation:
—: no threading
∓: tendency of threading is very slight observed.
±: threading is slightly observed.
+: completely threading.
++: Greatly threading.
(Note 2): The product of this invention was the product obtained in Example 5.
(Note 3): The experiment was carried out by placing the "kamaboko" on a wrap and also in a state of lightly placing a wrap on the "kamaboko".

As shown in Table 14 above, it can be seen that in the controls each added with water or ethyl acetate, slight threading was already observed after 3 days and complete threading was observed after 4 days but in the products added with the scavenger of the present invention, the tendency of forming very slight threading was unobserved after 6 days even in the case of adding 0.01% the scavenger of this invention, which showed the addition of 0.01% the scavenger had the effect of prolonging 2 days of preservation (complete threading was observed after 7 days). Also, it can be seen that in the product added with 1.0% or 0.1% the scavenger of the present invention, very slightly threading was observed after 9 days in the case of adding 1.0% and after 7 days in the case of adding 0.1%, which showed that the preservative effect of the scavenger of the present invention was very high. In addition, in the latter products, complete threading was observed during the days of the experiment.

When the bacteria of causing threading by staling were identified, it was confirmed that the bacteria were bacterial of the genus Bacillus. As the results, it was confirmed that the scavenger of the present invention was effective against putrefying bacteria.

In the products such as "kamaboko", it is useful that the occurrence of putrefaction prolongs even one day and hence as in the case of using the scavenger of the present invention, the occurrence of putrefaction is prolonged to 4 days even by the addition of 0.1% thereof, which confirms the very usefulness and effectiveness of the scavenger of this invention.

Also, in the control sample and the "kamaboko" added with 0.01% the scavenger of the present invention, the growth of mold was observed on the surfaces thereof after 8 days, while in the "kamaboko" added with 1.0% the scavenger of this invention and 0.1% the scavenger of this invention, the growth of mold was not yet observed after 8 days. However, even in the "kamaboko" added with 0.1% the scavenger of this invention, the growth of mold was first observed after 9 days and in the "kamaboko" added with 1.0% the scavenger of this invention, the growth of mold was first observed after 11 days.

Furthermore, when these samples were allowed to stand as they were, in the control sample added with 1% water, a large amount of Penicilliums of green spores having a diameter of from 4 to 8 mm and the colonies (1.0×2.3 cm) of mucor grew; in the control sample added with 1% ethyl acetate, the colonies (1.5×2.0 cm) of white mucor the colonies (15×18 cm) of Penicilliums of deep-green spores, the colonies of koji molds (Aspergillus) of yellow spores, and a large number of colonies of blue Penicilliums of green spores grew; in the sample added with 0.01% the scavenger of this invention, colonies (1.5×4.3 cm) of mucor, two colonies (1.0×0.8 cm) of Aspergillus, and a large number of colonies of Penicillium grew; and in the sample added with 0.1% the scavenger of this invention, colonies (1.2×3.0 cm) of mucor, colonies (diameter: 0.8 cm) of Aspergillus, and a large number of colonies of Penicillium of green spores grew. Meanwhile, in the sample added with 1.0% the scavenger of this invention, only two colonies (diameter: about 4 mm) of Penicillium grew.

From the above results, it has been found that the scavenger of the present invention has an antimicrobial activity to not only bacteria but also molds.

Also, the food-keeping effect of the scavenger of the present invention was determined from the viewpoint of quality keeping of foods. The results are shown in Table 15 below.

TABLE 15

| Additive | Added Amount (%) | Solid Conc. of (A)* (ppm) | Term | Passed Days | | | | | | | | | | | |
|---|---|---|---|---|---|---|---|---|---|---|---|---|---|---|---|
| | | | | 1 | 2 | 3 | 4 | 5 | 6 | 7 | 8 | 9 | 10 | 11 | 12 |
| Water** | 1.0 | — | Color | — | ± | ± | + | + | + | + | + | + | + | + | + |
| | | | Springiness | — | — | ± | ± | + | + | + | + | + | + | + | + |
| Ethyl Acetate** | 1.0 | — | Color | — | ± | ± | + | + | + | + | + | + | + | + | + |
| | | | Springiness | — | — | ± | ± | ± | + | + | + | + | + | + | + |
| (A)* | 1.0 | 450 | Color | — | — | — | — | — | — | — | — | ± | ± | ± | ± |
| | | | Springiness | — | — | — | — | — | — | — | ± | ± | ± | + | + |
| (A)* | 0.1 | 45 | Color | — | — | — | — | — | — | ± | ± | ± | + | + | + |
| | | | Springiness | — | — | — | — | — | — | ± | ± | + | + | + | + |

TABLE 15-continued

| Additive | Added Amount (%) | Solid Conc. of (A)* (ppm) | Term | Passed Days | | | | | | | | | | | |
|---|---|---|---|---|---|---|---|---|---|---|---|---|---|---|---|
| | | | | 1 | 2 | 3 | 4 | 5 | 6 | 7 | 8 | 9 | 10 | 11 | 12 |
| (A)* | 0.01 | 4.5 | Color | − | − | − | ± | ± | ± | + | + | + | + | + | + |
| | | | Springiness | − | − | ± | ± | ± | ± | + | + | + | + | + | + |

*Scavenger of the Invention
**Control
In Table 15:
(Note 1): Evaluation method:
Color:
− White
± Slightly brown
+ Brown
Springiness:
− High springiness
± Slightly inferior springiness
+ No springiness
(Note 2): The scavenger of this invention was the product obtained in Example 5.
(Note 3): The experiment was carried out in the state that a wrap was placed under the "kamaboko" and a wrap was lightly covered thereon.

As shown in Table 15, in the controls without the scavenger of the present invention, in the case of storing the food at room temperature without completely sealing it, the springiness already becomes inferior after 2 days and loses its commercial value, while in the samples added with the scavenger of this invention, the sample added with 0.1% the scavenger keeps the springiness and freshness until the 6th day and the sample added with 1.0% the scavenger keeps its springiness and freshness until the 7th day, which shows that the scavenger of the present invention has a remarkable food quality keeping effect. In addition, with the increase of the springiness of the food, the food shows more freshness, which shows that there is a correlation between the springiness and the freshness of food.

Also, as to the color of the surface of the food, as shown in Table 15, it can be seen that in the sample added with 0.1% the scavenger of this invention, the time of causing browning is delayed 2 days and the sample added with 0.1% or 1.0% the scavenger of this invention, the time of causing browning is delayed 5 to 6 days.

From these results described above, it has been found that in the recent requirement for keeping food, in particular, for keeping an additive-free food in a fresh state, the food-keeping effect of the scavenger of this invention is very effective. In particular, for a daily food, wherein the freshness is most important, and having a short relish time, such as "kamaboko" used in the foregoing experiments, prolonging of one day of the relish time is said to become a large power for winning the goods competition in the production, transporting, sale, and consumption of the goods and it can be said to be socially very useful that the food-keeping effect is prolonged several days as in the case of using the scavenger of the present invention.

Figure 13:
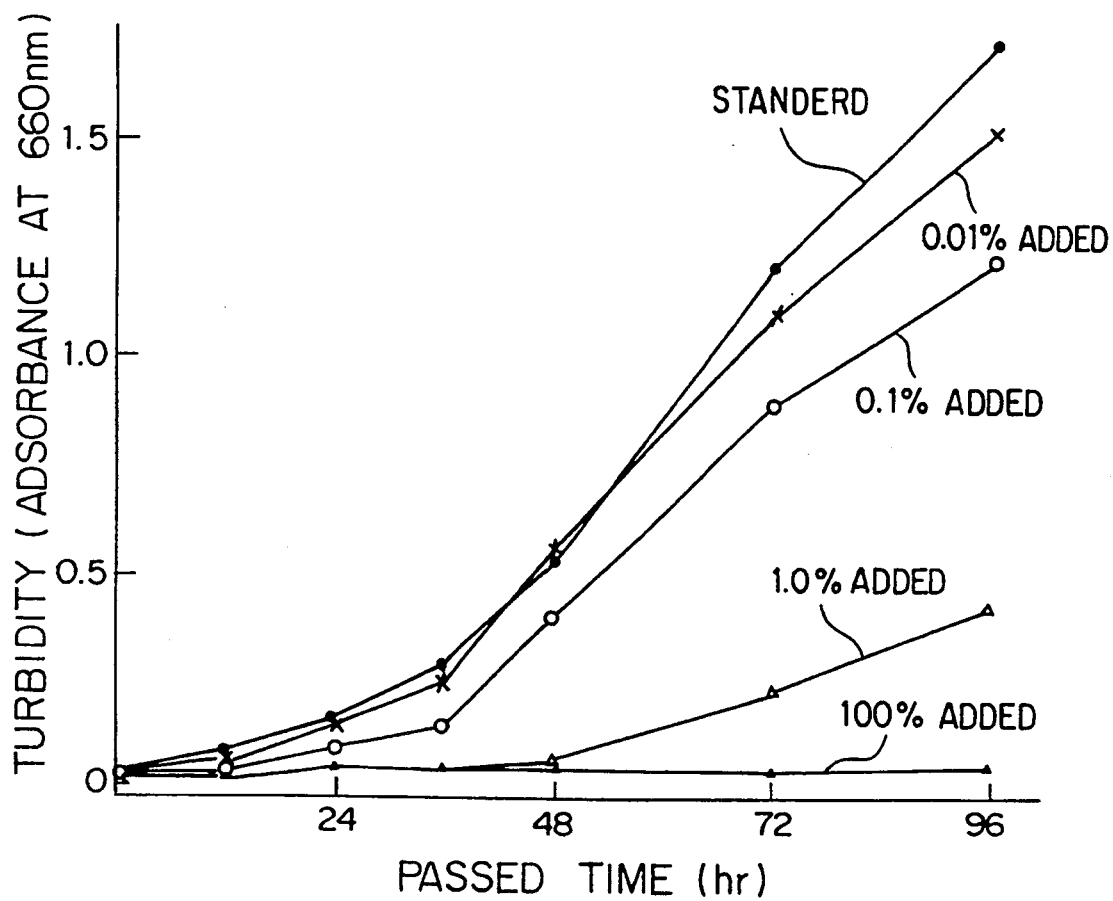
FIG. 13 is a graph showing the result of determining the storage effect by the scavenger of the present invention in a sweet drink made from fermented rice (amazake).

Then, about a sweet beverage made from fermented rice "amazake" which is a typical food having a large glucide content, the food-keeping effect of the scavenger of the present invention was determined on "amazake" supplemented with 10 0%, 10% 0 1% or 0.01% of the scavenger of this invention. The results thereof with the passage of time are shown in FIG. 13. In addition, the "amazake" used in this case was not heat-sterilized and the scavenger of this invention used was the product obtained in Example 1. Also, for measuring the turbidity of the "amazake" solid matters were removed therefrom by filtration and the measurement was carried out in an open system of a wide-mouthed bottle.

In the case of "amazake" without being supplemented with the scavenger of this invention, the turbidity thereof began to increase after 12 hours and after allowing "amazake" to stand for 24 hours, the absorbance at 660 nm. became 0.170, which showed a considerable increase of turbidity, while in the "amazake" supplemented with 0.01% of the scavenger of this invention, a significant difference was not observed as compared with the control sample but in the "amazake" with 0.1% the scavenger of this invention added, the increase of turbidity was not observed in the stage of allowing to stand it for 12 hours and also growth of bacteria since then was clearly restrained as compared with the control sample. Also, in the "amazake" supplemented with 1.0% of the scavenger of this invention, it could be seen that the too much increase of turbidity was not observed at the stage of allowing to stand it for 48 hours and the growth of bacteria since then was considerably restrained. From the foregoing facts, it could be seen that by the addition of 1.0% the scavenger of this invention to "amazake", the food-keeping effect of at least 36 hours was obtained and thus the scavenger of this invention was very effective.

Also, when pH of these "amazakes" was measured, in the control sample without containing the scavenger of this invention, pH thereof became lower than 3.0 after allowing to stand for 72 hours, while in the sample added with 1.0% the scavenger of this invention, pH was not changed much after allowing to stand for 72 hours and pH became 5.70 even after allowing to stand for 96 hours. by the change of pH, in the control sample without containing the scavenger of this invention, the increase of turbidity by contamination with microorganisms was confirmed and also in the sample added with 1.0% the scavenger of this invention, prolonging of the quality-keeping time of longer than 2 days was confirmed.

Furthermore, for knowing the cause of the occurrence of turbidity in the control sample and the samples supplemented with 1.0% and 00.1% the scavenger of this invention, a part of each liquid sample was sampled and observed with a microscope, whereby it could be confirmed that the turbidity was caused by yeast.

Also, in the "amazakes" without being supplemented with the scavenger of this invention and those supplemented with 0.1% and 0.01% of the scavenger, the formation of a film-like matter on the surface of the liquid was observed after 2 days. However, in the "amazake" supplemented with 1.0% or more of the scavenger of this invention, the formation of such a film-like matter on the surface thereof was not observed as far as the observation before 4 days. As the result of the observation with a microscope, the foregoing film-like matter was found to be yeast and as the results described above, it has been confirmed that the scavenger of the present invention has an antimicrobial activity to yeast. By the fact that such an inhibition effect was confirmed in a material such as "amazake" which was very liable to be putrefied and could be used as a culture medium for microorganism, it was confirmed that the scavenger of the present invention was also very excellent for practical use.

Also, in the sample added with 10% the scavenger of the present invention, the sample was not contaminated with microorganisms and no turbidity occurred during testing of 4 days. In addition, when the change of the sample was further observed after the test, no turbidity was observed even after 12 days. Thus, it has been confirmed that the food-keeping effect of the scavenger of this invention for "amazake" is very remarkable. As to the odor of the sample, the sample gave no acid smell.

Furthermore, when pH of the sample supplemented with 10% the scavenger of this invention was measured, no change of pH was observed after 5 days and thus it was also confirmed from pH that the sample was not putrefied.

From the aforesaid facts, the epoch-making result that in the "amazake" added with 10% the scavenger of this invention, the growth of microorganisms could be prevented longer than 12 days.

Accordingly, it is clear that the scavenger of the present invention has a food-keeping effect (putrefaction inhibition effect). As described above, in "amazake" which is not heat-sterilized and is liable to putrefy, the life as goods can be prolonged longer than 1.5 days (36 hours), which are high antiseptic and antimicrobial effects and show the effectiveness of the scavenger of this invention as a preservative.

Furthermore, the scavenger of the present invention is effective as a freshness-keeping agent for vegetables, fishes, etc. The result of carrying out a test by spraying the scavenger of this invention onto a lettuce is as follows.

When water was sprayed onto a lettuce and the lettuce was allowed to stand at room temperature, the lettuce was bent after 12 hours and the wound was browned after 2 days. However, in the lettuce sprayed with the scavenger of this invention diluted 50 times with water, the lettuce kept the freshness even after 20 hours and was not discolored up to the 4th day.

The invention will now be described more practically by the following examples, wherein all parts and percentages are by weight.

EXAMPLE 1

After grinding well 15 kg of polished rice, 45 liters of warm water of 60° C. and 50 g of liquefying amylase were added thereto followed by stirring well. Thereafter, the temperature of the mixture was gradually raised to boiling and extracting for 5 minutes, and the extract was cooled to 30° C. Thereafter, the extract was pressed by a pressing apparatus, and 41 liters of a pressed liquid (the scavenger of this invention) and 16 g of a residue were obtained.

EXAMPLE 2

After grinding well 1 kg of polished rice, 5 liters of an aqueous 0.1% hydrochloric acid solution was added thereto followed by stirring well, and the mixture was allowed to stand for 6 hours. Thereafter, the mixture was pressed by a pressing apparatus to provide 4.6 liters of a pressed liquid and 1.2 kg of a residue. By neutralizing the pressed liquid with an aqueous 1N sodium hydroxide solution, 4.7 liters of the scavenger (product) of this invention was obtained.

EXAMPLE 3

After grinding 1 kg of polished rice, 3 liters of 95% ethanol was added thereto followed by stirring well and the mixture was allowed to stand for 4 days. Thereafter, the mixture was pressed by a pressing apparatus to provide 2.5 liters of a pressed liquid and 1.2 kg of a residue. To one liter of the pressed liquid was added 500 ml of water and then ethanol was completely removed therefrom by means of a rotary evaporator to provide 480 ml of the scavenger (product) of this invention.

EXAMPLE 4

After adding 10 ml of a cultured yeast solution to one liter of the water extract obtained in Example 1, the mixture was kept at a temperature of 25° C. to carry out the alcoholic fermentation for 4 days. Thereafter, the fermented product was filtered to provide 940 ml of the scavenger (product) of this invention.

EXAMPLE 5

The pressed liquid obtained in Example 1 was acidified by the addition of hydrochloric acid and the acidified product was extracted was extracted with ethyl acetate to remove dextrin. Thereafter, ethyl acetate was volatilized off and the residue was dissolved in water to provide 750 ml of the scavenger (product) of this invention.

EXAMPLE 6

After mixing 10 liters of the product of this invention obtained in Example 5 and 6 kg of dextrin, the mixture was spray dried to provide 7 kg of a powder. The powder obtained can be used as an antiulcer agent and a preservative.

EXAMPLE 7

A mixture of 30% (by weight) of the product of this invention obtained in Example 5, 2.0% stearic acid, 0.5% cetanol, 2.0% lanolin, 2.0% isopropyl myristate, 3.0% squalene, 8.0% fluid paraffin, 1.7% polyoxyethylene cetyl ether, 0.8% sorbitan monostearate, and 0.2% vitamin A acetic acid ester was heated to about 75° C. to form a solution and then 1.0% triethanolamine, 4.0% glycerol, 0.3% a perfume and antiseptics, and 44.5% water were added to the solution by heating to about 75° C. with stirring to provide a milk lotion.

EXAMPLE 8

To a mixture of 30.0% the product obtained in Example 1, 3.0% of sorbitol, 5.0% glycerol, and 41.0% water were added 0.1% allantoin, 0.5% a polyoxyethylene-cured castor oil derivative, 20.0% ethanol, and 0.4% a perfume with stirring to form a homogeneous solution. The solution obtained can be used as a face lotion.

EXAMPLE 9

A mixture of 15.0% beeswax, 31.0% vaseline, 20.0% fluid paraffin, 4.0% sorbitan sesquioleate, and 2.0% ethyl p-aminobenzoate was heated to about 75° C. to form a solution and then 10.0% the product obtained in Example 1, 1.0% a perfume, 0.4% an antioxidant and antiseptics, and 16.6% water were added to the solution by heating to about 75° C. with stirring followed by cooling to provide a cosmetic sunscreen.

EXAMPLE 10

After dissolving 20.9% polyethylene glycol 4000 in 29.9% polyethylene glycol 400 by heating to 65° C. on a hot-water bath, 40.0% of the product of this invention obtained in Example 1 and 0.2% an acrinol fine powder were added to the solution followed by stirring and cooling to provide an ointment.

EXAMPLE 11

A mixture of 24.0% myristic acid, 2.0% stearic acid K, 10.0% N-lauroylmethyltarine sodium, 2.0% P.O.E. sorbit tetraoleate, 4.0% coconut oil fatty acid, 2.0% avocado oil, and 10.0% glycerol was heated to 75° C. to form a solution and the solution was placed in a mixing tank. The pressure in the mixing tank was reduced not higher than 70 cm Hg and an aqueous solution prepared by dissolving 5.5% potassium hydroxide in 19.0% purified water in a dissolver by heating to 50° C. was added to the solution to carry out a saponification. After the saponification, 11.2% purified water and 10.0% the product of this invention obtained in Example 1 were added to the saponified mixture followed by cooling and stirring, 0.3% a perfume was added thereto at 50° C., and after cooling the mixture to 35° C., stirring was stopped. The mixture was kept at 40° C. for 48 hours to carry out curing to provide a face-washing foam.

EXAMPLE 12

A mixture of 21% polyoxyethylene lauryl sodium sulfate, 7% coconut oil fatty acid amide propylbetaine, 2% lauryldimethylamine oxide, and 3% coconut oil fatty acid diethanolamide was heated to 70° C. with stirring to form a transparent liquid. Then, 20% the product of this invention obtained in Example 1 and 47% purified water were added to the liquid and the mixture was cooled to 30° C. with stirring to provide a kitchen detergent.

EXAMPLE 13

A mixture of 10% sodium hydrogenated glyceryl cocoate sulfate, 10% P.O.E.(3) alkyl ether sodium acetate, 20% 2-alkyl-N-carboxymethyl-N-hydroxyethylimidazolium betaine, 0.2% paraben, and 30% purified water was heated to 70° C. with stirring to form a transparent liquid. Then, after adding thereto 15% the product of this invention obtained in Example 1, the resultant mixture was allowed to cool, 0.5% a perfume and 14.3 purified water were added thereto at 45° C., and the resultant mixture was stirred for about one hour at room temperature to provide a body soap.

EXAMPLE 14

After melting 1% polyoxyethylene hydrogenated castor oil by heating to 60° C., 1% a perfume was added thereto followed by stirring well, and 98% the product of this invention obtained in Example 1 was added to the mixture followed by stirring to provide a bath product.

We claim:

1. A method of preparing an extract of rice which is effective as a scavenger of active oxygen, which comprises:
   adding water to rice in the amount of from 2 to 5 times by volume the amount of the rice;
   pretreating the water and rice mixture with an acid or an alkali;
   allowing the mixture to stand at a temperature not higher than 40° C.;
   compressing the resultant mixture; and
   recovering the liquid obtained.

2. A method as claimed in claim 1, wherein the rice is ground or powdered before adding the water.

3. A method as claimed in claim 1, further comprising subjecting the recovered liquid to fermentation to produce alcohol or lactic acid.

4. A method of preparing an extract of rice which is effective as a scavenger of active oxygen, which comprises:
   adding water in an amount of from 2 to 5 times by volume the amount of the rice;
   pretreating the water and rice mixture with amylase;
   heating the mixture to a temperature of about 40° C. to its boiling point;
   compressing the resultant mixture; and
   recovering the liquid obtained.

5. A method as claimed in claim 4, wherein the rice is ground or powdered before adding the water.

6. A method as claimed in claim 4, further comprising subjecting the recovered liquid to fermentation to produce alcohol or lactic acid.

7. A method of preparing an extract of rice which is effective as a scavenger of active oxygen, which comprises subjecting rice to an extraction with an organic solvent, allowing the mixture to stand at room temperature for about 4 days, compressing the resultant mixture and recovering the liquid obtained.

8. A method as claimed in claim 7, wherein the rice is ground or powdered before adding the organic solvent.

9. A method as claimed in claim 7, wherein the organic solvent is ethanol.

10. A method as claimed in claim 7, further comprising subjecting the recovered liquid to fermentation to produce alcohol or lactic acid.

11. The rice extract which is useful as an active oxygen scavenger, produced by the method of any one of claim 1, 4 and 7.

12. A medicament composition containing the extract as claimed in claim 11 and a pharmaceutically acceptable carrier.

13. A cosmetic containing the extract as claimed in claim 11.

14. A food containing the extract as claimed in claim 11.

15. A method of scavenging active oxygen in a mammal in need of lowering the active oxygen in its body which comprises administering an effective amount of the medicament as claimed in claim 12.

16. A method of scavenging active oxygen in a mammal in need of lowering the active oxygen in its body which comprises administering an effective amount of the cosmetic as claimed in claim 13.

17. A method of scavenging active oxygen in a mammal in need of lowering the active oxygen in its body which comprises administering an effective amount of the food as claimed in claim 14.

* * * * *